United States Patent [19]

LaHann

[11] 4,313,958

[45] Feb. 2, 1982

[54] METHOD OF PRODUCING ANALGESIA

[75] Inventor: Thomas R. LaHann, Cleves, Ohio

[73] Assignee: The Procter & Gamble Company, Cincinnati, Ohio

[21] Appl. No.: 200,102

[22] Filed: Oct. 24, 1980

[51] Int. Cl.$^3$ ............................................ A61K 31/165
[52] U.S. Cl. ................................................... 424/324
[58] Field of Search ........................................ 424/324

[56]  References Cited

PUBLICATIONS

J. S. Kiernan, Quart. J. of Exp. Physiol., (1977) 62 151–161.
Jansco, et al., Br. J. Pharmac. Chemother. (1967), 31, 138–151.
Arvier, et al., Br. J. Pharm. (1977), 59, 61–68.

Primary Examiner—Stanley J. Friedman
Attorney, Agent, or Firm—Michael J. Roth; Steven J. Goldstein; Richard C. Witte

[57] ABSTRACT

Capsaicin (8-methyl-N-vanillyl-6-noneanamide) is a useful, potent analgesic.

6 Claims, No Drawings

METHOD OF PRODUCING ANALGESIA

TECHNICAL FIELD

This invention relates to the use of capsaicin (8-methyl-N-vanillyl-6-nonenamide) to produce analgesia.

In general, analgesics fall into two broad categories. The simple analgesics, such as aspirin, are most effective against pain of integumental origin, headache, and muscle ache; the narcotics are more useful for deep or visceral pain. Narcotic analgesics such as morphine produce more profound effects than simple analgesics, and are potentially addicting, with the development of tolerance and physical dependence. The morphine-like analgesics appear to work through interaction with the endorphin/enkephalin system of the CNS; many, if not all of the simple, non-narcotic analgesics appear to work by inhibition of prostaglandin synthetase. The effect of narcotics is to elevate the pain threshold above the normal level; the non-narcotic analgesics act to raise an abnormally low pain threshold to the normal level. The narcotic analgesics are antagonized by compounds such as naloxone; the non-narcotic analgesics are not.

The present invention relates to the discovery that capsaicin, the pungent component of paprika, is a potent analgesic. In this action, it appears to be largely unrelated to the two known classes of analgesics. In certain tests, it produces a level of analgesia comparable to morphine, yet it is not antagonized by classical narcotic antagonists, such as naloxone. It effectively prevents the development of cutaneous hyperalgesia, but appears to have minimal effects on normal pain responses at moderate doses. At high doses capsaicin also exerts analgesic activity in classical models of deep pain, elevating the pain threshold above the normal value.

BACKGROUND ART

J. A. Kiernan, *Quart. J. of Exp. Physiol.*, (1977) 62 151–161, states that capsaicin is known to confer resistance to certain chemical irritants.

Jancso, et al., *Br. J. Pharmac. Chemother.* (1967), 31, 138–151, states that by repeated administration of capsaicin, ocular and/or cutaneous pain receptors can be desensitized to chemical, but not other, stimuli.

Arvier, et al., *Br. J. Pharm.* (1977), 59, 61–68, indicate that capsaicin reduces or blocks the edema formation associated with certain types of inflammation.

DISCLOSURE OF THE INVENTION

The present invention provides a method for treating pain in humans and lower animals in need of such treatment, comprising administering to the human or lower animal a safe and effective amount of capsaicin.

Capsaicin has the following structure:

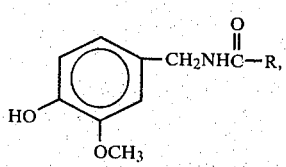

where R is $-(CH_2)_4\ CH=CH-CH\ (CH_3)_2$

Capsaicin can be readily obtained by the ethanol extraction of the fruit of *capsicum frutescens* or *capsicum annum*. It is available commercially from a variety of suppliers, and can also be prepared synthetically by published methods. In some commercially available forms of capsaicin, $R = -(CH_2)_7CH_3$. This "pseudocapsaicin" is pharmacologically indistinguishable from natural capsaicin. The present invention encompasses the use of both forms, and where the term "capsaicin" is used, both forms are meant.

In the practice of this invention, the capsaicin can be administered either topically or systemically.

By "topical administration" herein is meant directly laying or spreading on epidermal or epithelial tissue, especially skin.

By "safe and effective amount" of capsaicin is meant a sufficient amount of capsaicin to alleviate or prevent the pain being treated at a reasonable benefit/risk ratio attendant with any medical treatment. Within the scope of sound medical judgment, the amount of capsaicin used will vary with the particular condition being treated, the severity of the condition, the duration of the treatment, the specific formulation employed and the concentration of capsaicin therein, and like factors within the specific knowledge and expertise of the patient or the attending physician.

By "systemic administration" herein is meant introducing the capsaicin into the tissues of the body, other than by the oral route. Systemic administration thus includes, without limitation, intrathecal, epidural, intramuscular, intravenous, intraperitoneal, and subcutaneous administration. Capsaicin does not appear to be active when administered orally, and therefore "systemic administration" when used herein does not include oral administration.

The vascular and respiratory side effects of intravenous and intra-arterial capsaicin as well documented. See, for example, C. C. Ton, et al., *Br. J. Pharmacol.*, (1955), 10, 175–182, "The Pharmacological Actions of Capsaicin and Analogs" and R. M. Virus and G. F. Geonart, *Life Sciences*, 25, 1273 (1979), "Minireview - The Pharmacologic Actions of Capsaicin: Apparent Involvement of Substance P and Serotonin", the disclosures of which are fully incorporated herein by reference. These side effects should be kept in mind when capsaicin is administered intravascularly. Because these side effects are reduced or absent when capsaicin is administered by other routes, administration of capsaicin by the intravascular route is a less preferred embodiment of this invention.

INDUSTRIAL APPLICABILITY

The broad range of analgesic benefits obtainable by the practice of this invention can be readily appreciated by reference to the following animal experiments.

RAT RADIANT HEAT TESTING PROCEDURE

Male Sprague-Dawley rats weighing between 115 and 135 grams were used. Capsaicin was administered via subcutaneous injection 1–2 days prior to test initiation. The rats were injected with increasing doses of capsaicin, with at least 2 hours elapsing between each injection. (This "stairstep" dose pattern tends to reduce or eliminate some of capsaicin's side effects, and is therefore especially preferred.) Approximately 24 hours prior to initiation of the experiment, the rats' lower backs were clipped and treated with a commercial depilatory.

Within 2 hours of depilation, and again 3 hours prior to pain testing, the rats were exposed to ultraviolet radiation. Exposure to the ultraviolet radiation induced a hyperalgesic state (sunburn), where stimuli previously not felt as pain were perceived to be painful.

In the pain testing, the rats were exposed to a heat stimulus (radiant heater) until a visible flinching movement of the skin was observed, or, to prevent physical injury, until a predetermined cut-off time was reached. The exposure time required to elicit this "skin-twitch" is a measure of the pain threshold. Analgesic activity was measured by the increase in time required to elicit the skin twitch in treated animals versus controls.

Results

Typical results are shown in Table 1. Animals which are not exposed to ultraviolet radiation typically exhibit reaction times on the order of 3-4 seconds. Ultraviolet light irradiated animals typically have reaction times on the order of 1.7-2.0 seconds. This difference in reaction times is an index of hyperalgesia. Nonsteroidal anti-inflammatory agents act, at high doses, to elevate the pain threshold to near normal levels. Even moderately toxic doses of these agents, however, will not elevate the pain threshold above the normal (3-4 seconds) level. The narcotic analgesic agent morphine sulfate also antagonizes the induced hyperalgesic state and, at higher doses, elevates the pain threshold above the normal level.

Capsaicin, when delivered systemically in moderate doses (final dose of 25 mg/kg or less) prior to the ultraviolet irradiation, prevented the radiation induced hyperalgesia but did not elevate the pain threshold above the normal range. Larger doses of capsaicin systemically administered (final dose of 50 mg/kg or greater) elevated the pain threshold. Repeated topical application of capsaicin prior to the ultraviolet irradiation also prevented development of a hyperalgesic state (Table 2).

TABLE 1

| Treatment | % of 0-Time Control Response | | | |
|---|---|---|---|---|
| | 0 hr | 0.5 hr | 1.5 hr | 2.5 hr |
| Vehicle Control | 100 | 94 | 88 | 93 |
| Capsaicin, 3 injections (4,8,15 mg/kg) | 135* | 145* | 142* | 179* |
| Capsaicin, 4 injections (4,8,15,25 mg/kg) | 179* | 185* | 198* | 208* |

*$P < 0.01$
All injections made between −24 and −48 hr time points
An elevation of 175-200% over the control response time reflects a total suppression of the hyperalgesic state

TABLE 2

| Treatment | % of 0-Time Control Response | | | |
|---|---|---|---|---|
| | 0 hr | 1 hr | 2 hr | 3 hr |
| Control | 100 | 104 | 101 | 96 |
| Capsaicin, topical | 126* | 137* | 153* | 172* |

TABLE 2-continued

| Treatment | % of 0-Time Control Response | | | |
|---|---|---|---|---|
| | 0 hr | 1 hr | 2 hr | 3 hr |
| (8 applications) | | | | |

*$P < 0.01$
Topical treatments applied between the −72 and −16 hr time points acetaminophen (450 mg/kg) immediately prior to testing show little or no change from this baseline. Morphine sulfate, administered i.p. immediately prior to testing, exhibits significant analgesic activity (Table 4). Capsaicin-induced analgesia differs from that induced by morphine in that capsaicin-treated animals remain analgesic for 7-10 days while in morphine-treated animals the analgesia lasts 4-6 hours. These results show that capsaicin elicits a prolonged analgesia of a magnitude similar to that elicited with large doses of morphine.

Mouse Hot Plate Tests

The MHP model system is designed to detect and evaluate agents which elevate the threshold for the perception of pain. Classically, this method has been utilized primarily to evaluate narcotic type analgesic agents. Unless administered in toxic quantities, nonsteroidal anti-inflammatory agents exhibit little or no activity in this system.

Male CF-1 mice were used. Animals were divided into groups of ten and then tested on the "hot plate" to determine their predrug response times. Each animal was then tested with either capsaicin or a control. Capsaicin was administered via intraperitoneal (i.p.) injection 1 day prior to test initiation. Animals were injected with sequentially increasing doses of capsaicin, with at least 2 hours elapsing between each injection.

Procedure

The mice were placed on a 55° C. heated surface and their responses were observed. The endpoint is either a rapid fanning or licking of a paw. To prevent physical injury, the animals were not allowed to remain in contact with the heated surface for more than 30 seconds. The exposure time required to elicit the endpoint response is a measure of the pain threshold. The difference in time required to elicit the endpoint response before and after drug treatment provides a measure of analgesia. The increase in time required to elicit the endpoint response in treated animals versus controls is a second measure.

Results

Results are shown in Table 3. Naive or control animals typically exhibit reaction times on the order of 4.8 seconds. Mice orally gavaged with acetylsalicylic acid (360 mg/kg) or acetaminophen (450 mg/kg) immediately prior to testing show little or no change from this baseline. Morphine sulfate, administered i.p. immediately prior to testing, exhibits significant analgesic activity (Table 4). Capsaicin-induced analgesia differs from that induced by morphine in that capsaicin-treated animals remain analgesic for 7-10 days while in morphine-treated animals the analgesia lasts 4-6 hours.

These results show that capsaicin elicits a prolonged analgesia of a magnitude similar to that elicited with large doses of morphine.

TABLE 3

| DRUG | No. OF DOSES | DOSE SEQUENCE (mg/kg) | AVG. PREDRUG RESPONSE TIME (sec) | AVG. POST-DRUG RESPONSE TIME (sec) |
|---|---|---|---|---|
| Vehicle | Control | — | 4.9 | 4.8 |
| CAPSAICIN | 1 | 4 | 4.9 | 5.1 |
| CAPSAICIN | 2 | 4,8 | 4.9 | 7.8 |
| CAPSAICIN | 3 | 4,8,15 | 4.8 | 11.3 |

TABLE 3-continued

| DRUG | No. OF DOSES | DOSE SEQUENCE (mg/kg) | AVG. PREDRUG RESPONSE TIME (sec) | AVG. POST-DRUG RESPONSE TIME (sec) |
|---|---|---|---|---|
| CAPSAICIN | 4 | 4,8,15,25 | 4.9 | 13.4 |
| CAPSAICIN | 5 | 4,8,15,25,50 | 4.8 | 28.8 |
| CAPSAICIN | 6 | 4,8,15,25,50,100 | 4.9 | >30 |

TABLE 4

| DRUG | DOSE SEQUENCE (mg/kg) | AVG. PREDRUG RESPONSE TIME (sec) | AVG. POST-DRUG RESPONSE TIME (sec) |
|---|---|---|---|
| VEHICLE CONTROL | — | 4.9 | 5.1 |
| Morphine Sulfate | 7 | 4.9 | 6.9 |
| Morphine Sulfate | 10 | 5.0 | 9.0 |
| Morphine Sulfate | 25 | 4.9 | 23.6 |

Phenylquinone Writhing Tests

The model is designed to detect analgesic activity, whether produced by narcotic type analgesic agents or nonsteroidal anti-inflammatory drugs.

Male Sprague-Dawley rats weighing between 125 and 175 grams were used. Animals were divided into groups and each group was injected with either the test compound or its vehicle control. Animals were injected with capsaicin 1-2 days prior to test initiation, the capsaicin being administered in sequentially increasing doses with at least 2 hours elapsing between injections.

All animals received an intraperitoneal injection of phenylquinone (3 mg/kg) and then were closely observed for the next 10 minutes. The percent of treated animals protected from the phenylquinone induced writhing is an index of the analgesic activity of the test compound. All animals not writhing within the 10 minute observation period are considered to be in a state of analgesia.

Results

The phenylquinone rapidly induced characteristic writhing responses in all control animals. Capsaicin exhibited analgesic activity in this system as evidenced by the dose response relationship shown in Table 5. Acetylsalicylic acid (aspirin) also exhibits analgesic activity in this sytem, as shown in Table 6. The total administered dose of capsaicin ranged from 27 mg/kg (4,8,15) to 102 mg/kg (4,8,15,25,50). When compared to aspirin these doses of capsaicin can be seen to be from 3 to 6 times as potent as equimolar doses of aspirin.

These results indicate that capsaicin elicits analgesia and, on a molar basis, is a much more potent analgesic agent than aspirin.

TABLE 5

| Drug | Route | No. of Injections | Dose Sequence (mg/kg) | % Animals Protected Against Writhing |
|---|---|---|---|---|
| Vehicle Control | i.p.* | 4 | — | 0 |
| Capsaicin | i.p. | 3 | 4,8,15 | 0 |
| Capsaicin | i.p. | 4 | 4,8,15,20 | 10 |
| Capsaicin | i.p. | 4 | 4,8,15,25 | 33 |
| Capsaicin | i.p. | 5 | 4,8,15,25,50 | 40 |
| Vehicle Control | s.c.** | 4 | — | 0 |
| Capsaicin | s.c. | 3 | 4,8,15 | 0 |
| Capsaicin | s.c. | 4 | 4,8,20 | 10 |
| Capsaicin | s.c. | 4 | 4,8,15,25 | 20 |
| Capsaicin | s.c. | 5 | 4,8,15,25,50 | 33 |

*Intraperitoneal
**Subcutaneous

TABLE 6

| Drug | Route | Dose (mg/kg) | % Animals Protected Against Writhing |
|---|---|---|---|
| Vehicle Control | Oral | — | 0 |
| Aspirin | Oral | 45 | 0 |
| Aspirin | Oral | 90 | 10 |
| Aspirin | Oral | 180 | 40 |
| Aspirin | Oral | 360 | 70 |

While the foregoing animal tests show dosage ranges of from 4 mg/kg to 100 mg/kg and total dosages of from 4 mg/kg to 202 mg/kg, these dosages, intended to most clearly show effect in the described model systems, are at the high end of the safe and effective dosage range. For clinical use, especially in humans, dosages of from 0.01 mg/kg to over 100 mg/kg and total doses of from 0.05 mg/kg to 1000 mg/kg are acceptable, and dosages of from 0.05 mg/kg to 250 mg/kg and total dosages of from 0.25 mg/kg to 500 mg/kg are preferred. Dosages of 0.1 mg/kg to 25 mg/kg and total dosages of from 0.5 mg/kg to 5 mg/kg are especially preferred. While dosages higher than the foregoing are effective, toxicity and side effects will present problems in some individuals.

What is claimed is:

1. A method for treating pain in humans and lower animals in need of such treatment, comprising administering to the human or lower animals a safe and effective amount of capsaicin.

2. A method according to claim 1 in which the capsaicin is administered topically.

3. A method according to claim 1 in which the capsaicin is administered systemically.

4. A method according to claim 3 in which the capsaicin is administered intramuscularly.

5. A method according to claim 3 in which the capsaicin is administered subcutaneously.

6. A method according to claim 3 in which the capsaicin is administered intraperitoneally.

* * * * *